(12) United States Patent
Charne

(10) Patent No.: US 6,323,392 B1
(45) Date of Patent: Nov. 27, 2001

(54) **FORMATION OF *BRASSICA NAPUS* $F_1$ HYBRID SEEDS WHICH EXHIBIT A HIGHLY ELEVATED OLEIC ACID CONTENT AND A REDUCED LINOLENIC ACID CONTENT IN THE ENDOGENOUSLY FORMED OIL OF THE SEEDS**

(75) Inventor: David G. Charne, Guelph (CA)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/259,346

(22) Filed: Mar. 1, 1999

(51) Int. Cl.$^7$ ............... A01H 1/02; A01H 1/04; A01H 1/06; C12P 7/64
(52) U.S. Cl. ............ 800/270; 800/306; 800/264; 800/274
(58) Field of Search ............... 800/264, 271, 800/274, 298, 303, 306, 270

(56) References Cited

U.S. PATENT DOCUMENTS 5,850,026 * 12/1998 DeBonte et al. .......... 800/281
6,169,190 * 1/2001 Lanuza et al. ............ 554/2

FOREIGN PATENT DOCUMENTS

WO92/03919 * 3/1992 (WO) ............ A01H/5/10
WO92/05251 * 4/1992 (WO) ............ C12N/15/11

OTHER PUBLICATIONS

Rankow et al. 1993, Profit summer rape. Canadian Journal of Plant Science 73:187–188.*
International Publication No. WO97/21340, "Plants Having Mutant Sequences That Confer Altered Fatty Acid Profiles", Applicant: Cargill Incorporated, Published: Jun. 19, 1997.
International Publication No. 97/30582, "Production of Hydroxylated Fatty Acids in Genetically Modified Plants", Applicant: Carnegie Institution of Washington, Published: Aug. 28, 1997.
International Publication No. 94/18337, "Altered Linolenic and Linoleic Acid Content in Plants", Applicant: Monsanto Company, Published: Aug. 18, 1994.
International Publication No. 92/03919, "Seeds, Plants and Oils With Altered Fatty Acid Profiles", Applicant: E.I. DuPont Nemours and Company, Published: Mar. 19, 1992.
Database BIOSIS, AN 199900123484, Tanhuanpaa et al., "Mapping and cloning of FAD2 gene to develop allele–specific PCR for oleic acid in spring turnip rape (Bassica rapa ssp. oleifera)", Molecular Breeding, vol. 4 (1998).
Hitz et al. Proceedings of the Ninth International Rapeseed Congress, Cambridge, UK, vol. 2, pp. 470–472, 1995.*
Kemble et al. Chapter 13, Seed Oils for the Future, American Oil Chemists' Society, Champaign, IL, pp. 136–141, 1992.*

* cited by examiner

Primary Examiner—David T. Fox
Assistant Examiner—David H. Kruse
(74) Attorney, Agent, or Firm—Burns, Doane, Swecker & Mathis, L.L.P.

(57) ABSTRACT

An improved route is provided for producing seeds capable of forming a *Brassica napus* $F_1$ hybrid via plant breeding wherein the vegetable oil of the seeds exhibits a highly elevated oleic acid (C18:1) content of at least 80 percent by weight (e.g. 80 to 86 percent by weight) and a reduced linolenic acid (C18:3) content of no more than 3 percent by weight (e.g. 1 to 3 percent by weight) based upon the total fatty acid content. The female parent plant (i.e., the seed parent) possesses a homozygous modified FAD-2 gene pair for elevated oleic acid production solely in either the A-genome or the C-genome, and the male parent (i.e, the pollen parent) possesses a homozygous modified FAD-2 gene pair for highly elevated oleic acid production in both the A-genome and the C-genome. Both parent plants also include at least one homozygous modified FAD-3 gene pair for reduced linolenic acid production. The seed yield depression commonly observed in the past in *Brassica napus* plants exhibiting a comparable highly elevated oleic acid concentration effectively is ameliorated in an efficient manner. The grower of the resulting seeds can produce a *Brassica napus* crop in improved yields wherein the endogenously formed oil of the seed harvest contains on average the desired elevated oleic acid content and reduced linolenic acid content. An endogenously formed *Brassica napus* oil is provided that is particularly well suited for use in frying applications. Such oil exhibits further stability in view of the low concentration of linolenic acid that concomitantly is produced within the seeds.

16 Claims, No Drawings

FORMATION OF *BRASSICA NAPUS* $F_1$ HYBRID SEEDS WHICH EXHIBIT A HIGHLY ELEVATED OLEIC ACID CONTENT AND A REDUCED LINOLENIC ACID CONTENT IN THE ENDOGENOUSLY FORMED OIL OF THE SEEDS

BACKGROUND OF THE INVENTION

Canola oil presently is commercially available which consists of approximately 6 percent saturated fatty acids primarily in the form of stearic acid (C18:0) and palmitic acid (C16:0), approximately 62 percent by weight oleic acid (C18:1) which contains a single double bond per molecule, approximately 22 percent by weight linoleic acid (C18:2) which contains two double bonds per molecule, approximately 10 percent by weight linolenic acid (C18:3) which contains three double bonds per molecule, and less than one percent by weight erucic acid (C22:1) which contains a single double bond per molecule.

Over the years scientists have worked to improve the fatty acid profile for rapeseed oil. Initially the erucic acid (C22:1) composition of rapeseed oil was reduced to produce what is often termed to be "canola" oil. The oxidative stability of the vegetable oil is related to the number of double bonds in its fatty acids. Molecules with several double bonds are recognized to be less stable. Thus, scientists also have worked to reduce the content of linolenic acid (C18:3) in order to improve shelf life and oxidative stability, particularly upon exposure to heat. This has not proved to be possible through the use of naturally occurring germplasm and the reported values for linolenic acid (C18:3) for such germplasm have been greater than 6 percent by weight (e.g., greater than 6 up to approximately 12 percent by weight). As reported by Gerhard Robbelen in Chapter 10 entitled "Changes and Limitations of Breeding for Improved Polyenic Fatty Acids Content in Rapeseed" from "Biotechnology for the Oils and Fats Industry" edited by Colin Ratledge, Peter Dawson, and James Rattray, American Oil Chemists' Society (1984), a mutagenesis experiment was able to achieve lines with less than approximately 3.5 percent by weight of linolenic acid (C18:3) based upon the total fatty acid content. The profiles of these lines indicated that nearly all of the linolenic acid was being directed to linoleic acid (C18:2) and that the levels of oleic acid (C18:1) increased only one or two percent. Nevertheless the oil appeared to offer some advantages over normal canola oil. For instance, the refining process required less hydrogenation than normal canola oil and it exhibited a superior fry life.

Studies have established the value of monounsaturated fatty acids as a dietary constituent. This has led to the popularization of the "Mediterranean Diet," with its emphasis on olive oil, a naturally occurring high source of oleic acid (C18:1). Such a diet is thought to avoid the problem of arteriosclerosis that results from the consumption of saturated fatty acids. However, even in this diet olive oil is thought to be less than ideal, due to its level of saturates. Canola oil is potentially a superior dietary oil, since it contains approximately one-half the saturated fat content of olive oil.

Mutagenesis techniques have been disclosed in the technical literature for increasing the oleic acid (C18:1) content of endogenously formed canola oil over that typically encountered. See in this regard the teachings of U.S. Pat. Nos. 5,625,130 and 5,638,637; European Patent No. 0323753; and International Publication Nos. WO90/10380 and WO92/03919.

Also, approaches involving genetic engineering have been utilized to modify the fatty acid profile of the oil that is endogenously formed in rapeseeds. See, for instance, International Publication No. WO 93/11245, and the Hitz et al. article appearing in the Proceedings of the Ninth International Rapeseed Congress, Cambridge, UK, Vol. 2, Pages 470 to 472 (1995).

Heretofore, it commonly has been observed that when a rape plant is provided that endogenously forms a vegetable oil having an oleic acid content (C18:1) of at least 80 percent by weight that such plant also exhibits less than optimum agronomic performance. Such reduced agronomic performance often is manifest by reduced plant vigor, a later flowering propensity, a lesser number of seed pods per plant, a lesser number of seeds per pod, a lesser overall plant yield, a smaller number of leaves per plant, a lesser total leaf area per plant, a lesser plant height, and a requirement for more time for the plant to reach full maturity. This reduced agronomic performance must be weighed against the improved character of the endogenously formed vegetable oil with respect to oleic acid production that is made possible by such plants.

It is an object of the present invention to provide an improved plant breeding process for forming *Brassica napus* $F_1$ hybrid seed having an enhanced commercial value attributable to a combination of (1) the atypical fatty acid profile of the endogenously formed seeds, and (2) the seed yield.

It is an object of the present invention to provide an improved plant breeding process for forming *Brassica napus* $F_1$ hybrid seed which exhibits a highly elevated oleic acid (C18:1) content.

It is a further object of the present invention to provide an improved process for forming *Brassica napus* $F_1$ hybrid seeds which exhibit a highly elevated oleic acid (C18:1) content and when planted can be grown to form rape plants associated with high oleic acid production which are free from the agronomic shortcomings commonly encountered in the prior art with rape plants that yield such an elevated oleic acid content.

These and other objects and advantages as well as the scope, nature, and utilization of the claimed invention will be apparent to those skilled in the art from the following detailed description and appended claims.

SUMMARY OF THE INVENTION

It has been found that an improved process for producing seeds capable of forming $F_1$ hybrid *Brassica napus* plants comprises:

(a) planting in pollinating proximity in a planting area parent plants (i) and (ii), wherein parent (i) is a *Brassica napus* plant possessing solely in either the A-genome or the C-genome a homozygous modified FAD-2 (i.e., oleate desaturase) gene pair that causes expression of an elevated oleic acid concentration in the endogenously formed oil of the seeds formed thereon, and further possesses at least one homozygous modified FAD-3 (i.e., linolate desaturase) gene pair that causes the expression of a reduced linolenic acid concentration in the endogenously formed oil of the seeds, and wherein parent (ii) is a *Brassica napus* plant possessing in each of the A-genome and the C-genome a homozygous modified FAD-2 gene pair that causes the expression of an elevated oleic acid concentration in the endogenously formed oil of the seeds formed thereon whereby oleic acid is formed in the endogenously formed oil of the seeds in a greater concentration than in the seeds of parent (i) under the same growing conditions, and further possesses at least one homozygous modified FAD-3 gene pair that results in a reduced linolenic acid concentration in the endogenously formed oil of the seeds formed thereon;

(b) growing *Brassica napus* plants resulting from the planting of step (a);

(c) preventing self-pollination of the plants of parent (i);

(d) transferring pollen between parent (ii) and parent (i); and (e) harvesting $F_1$ hybrid seeds produced on plants of parent (i) that are capable of forming *Brassica napus* plants that upon self-pollination form seeds possessing an endogenously formed vegetable oil having an oleic acid concentration of at least 80 percent by weight and which exceeds that of parent (i), a linolenic acid concentration of no more than 3 percent by weight, and wherein the resulting $F_1$ hybrid seeds when planted are capable of producing a crop in a yield that exceeds that of parent (i) and parent (ii) when each parent is pollinated by a pollen source possessing a genotype substantially the same as that of each parent plant and is grown under the same conditions.

DESCRIPTION OF THE PREFERRED EMBODIMENTS

The fatty acid concentrations discussed herein are determined in accordance with a standard procedure wherein the oil is removed from the *Brassica napus* oilseeds by crushing and is extracted as fatty acid methyl esters following reaction with methanol and sodium methoxide. Next the resulting ester is analyzed for fatty acid content by gas liquid chromatography using a capillary column which allows separation on the basis of the degree of unsaturation and chain length. This analysis procedure is described in the work of J. K. Daun et al, *J. Amer. Oil Chem. Soc.*, 60:1751–1754 (1983) which is herein incorporated by reference.

It is recognized that *Brassica napus* is a dibasic allotetraploid formed of two genomes (i.e., the A-genome and C-genome) and has a total of 38 chromosomes. The A-genome component is derived from *Brassica campestris* and consists of 20 chromosomes. The C-genome component is derived from *Brassica oleracea* and consists of 18 chromosomes.

When carrying out the process of the present invention, two parent plants described herein are planted in a planting area and are grown in pollinating proximity, self-pollination of the female parent plants (i.e., seed parent plants) is prevented, pollen is transferred from the male parent plants to the female parent plants to achieve fertilization, and $F_1$ hybrid seeds are formed thereon in a yield that exceeds that of both parent plants having an elevated oleic acid (C18:1) content of at least 80 percent by weight based upon the total fatty acid content in the endogenously formed vegetable oil of the seeds. "Pollinating proximity" is used herein to specify that the parent plants are grown in sufficient closeness to make possible the transfer of pollen while maintaining the viability of such pollen. The high oleic acid concentration of the vegetable oil is achieved through the concept of the present invention without sacrifice in agronomic properties.

The improved plant breeding process of the present invention involves the selection and utilization of specifically-defined *Brassica napus* parent plants. Such parent plants have been found through empirical research to be capable of yielding the advantageous results with respect to highly elevated oleic acid content and reduced linolenic acid content in the endogenously formed vegetable oil of the seeds combined with good agronomic performance which commonly was lacking in the prior art.

The *Brassica napus* female parent (i.e., the seed parent) selected for use in the hybridization process of the present invention possesses solely in either the A-genome or the C-genome a homozygous modified FAD-2 (i.e., oleate desaturase) gene pair that causes the expression of an elevated oleic acid (C18:1) concentration in the endogenously formed oil of the seeds combined with at least one homozygous modified FAD-3 (i.e., linolate desaturase) gene pair that causes the expression of a reduced linolenic acid (C18:3) concentration in the endogenously formed oil of the seeds. Such female parent commonly is selected that forms an oleic acid content of approximately 77 to 79 percent by weight based upon the total fatty acid content in the endogenously formed vegetable oil of the seeds. The vegetable oil oleic acid content of the female parent commonly will exceed that of the well-known Profit variety which possesses an unmodified FAD-2 gene pair by at least 14 percent (e.g., by 14 to 17 percent) by weight under the same growing conditions. The reference Profit variety was introduced by Agriculture Canada during 1989 and is known and publicly available. Seeds of the Profit variety can be obtained from Agriculture and Agri-Food Canada, Sakatoon, Saskatchewan, Canada. It has been found to be essential that the modified FAD-2 gene pair be present solely in either the A-genome or the C-genome so as to avoid the impairment of agronomic qualities that otherwise are observed if such modification were present in both genomes. The presence of the modified FAD-2 gene pair in both genomes (i.e., in the A-genome as well as in the C-genome) which leads to an even more highly elevated oleic acid production in the endogenously formed vegetable oil of the seeds commonly has been found to concomitantly impact adversely upon lipid loading throughout the plant including the cell membranes and to result in reduced agronomic performance as previously discussed. The presence of a modified FAD-2 gene pair solely in one genome can be confirmed by a oleic acid (C18:1) in the endogenously formed vegetable oil of the seeds of approximately 76 to 79 percent by weight based upon the total fatty acid content.

The *Brassica napus* male parent (i.e., the pollen parent) selected for use in the hybridization process of the present invention possesses in each of the A-genome and in the C-genome a homozygous modified FAD-2 gene pair that causes the expression of an elevated oleic acid concentration in the endogenously formed oil of the seeds in a greater concentration than in the seeds of the female parent. Such male parent commonly is selected that forms an oleic acid content of approximately 85 to 89 percent by weight based upon the total fatty acid content in the endogenously formed vegetable oil of the seeds. The vegetable oil oleic acid content of the male parent commonly will exceed that of the well-known Profit variety by at least 20 percent (by 20 to 25 percent) by weight under the same growing conditions. In view of the presence of the modified FAD-2 gene pair in both the A-genome and the C-genome, the overall agronomic qualities of the male parent are lesser than those of the female parent.

Parent plants possessing the modified genomes as discussed above can be formed by genetic engineering or the mutagenesis of conventional *Brassic napus* germplasm (e.g., existing canola varieties), or can be selected from previously available sources that already incorporate the requisite modified genomes as discussed herein. Once on hand, the requisite genes can be readily transferred by conventional plant breeding into other *Brassica napus* germplasms.

In a preferred embodiment when carrying out mutagenesis, one selects plant cells capable of regeneration (e.g., seeds, microspores, ovules, pollen, vegetative parts) from any of the oilseed *Brassica napus* varieties (e.g., canola) which are recognized to have superior agronomic characteristics. The *Brassica napus* plants may be of either the summer or winter types. The oilseed *Brassica napus* plant cells are subjected in at least one generation to mutagenesis, and an oilseed *Brassica napus* plant is regenerated from the cells to produce an oilseed plant and to form an oilseed in at least one subsequent generation that possesses the ability to form the atypical modified FAD-2 gene pair in the female parent and the atypical modified FAD-2 gene pairs in the male parent. Parent oilseed *Brassica napus* plants possessing the requisite FAD-2 gene pair(s) may be produced following mutagenesis via self-pollination for a sufficient number of generations (2 to 8 generations) to achieve substantial genetic homogeneity. Alternatively, the desired characteristics can be fixed through the formation of a new plant from a haploid microspore cell, causing the haploid to double, and producing a homozygous diploid plant in accordance with known techniques.

The mutagenesis preferably is accomplished by subjecting the plant cells (an oilseed) to a technique selected from the group consisting of contact with a chemical mutagen, gamma irradiation, and a combination of the foregoing, for a sufficient duration to accomplish the desired genetic modification but insufficient to completely destroy the viability of the cells and their ability to be regenerated into a plant. The *Brassica napus* oilseed preferably possesses a moisture content of approximately 5 to 6 percent by weight at the time of such mutagenesis. The mutagenesis may be accomplished by use of chemical means, such as by contact with ethylmethylsulfonate, ethylnitrosourea, etc., and by the use of physical means, such as x-rays, etc. The mutagenesis also may be carried out by gamma radiation, such as that supplied by a Cesium 137 source. The gamma radiation preferably is supplied to the plant cells (e.g., an oilseed) in a dosage of approximately 60 to 200 Krad., and most preferably in a dosage of approximately 60 to 90 Krad. It should be understood that even when operating at radiation dosages within the ranges specified, some plant cells (e.g., oilseeds) may completely lose their viability and must be discarded. See commonly assigned U.S. Pat. Nos. 5,625,130 and 5,638,637 which are herein incorporated by reference for a further discussion of the mutagenesis treatment.

When a mature *Brassica napus* halfseed is found to possess a desired mutation(s), the other halfseed, which will be genetically the same as the halfseed which was subjected to halfseed analysis, can next be caused to germinate and an oilseed *Brassica napus* plant is formed from the same and is allowed to undergo self-pollination. Such planting of the halfseed preferably also is carried out in a greenhouse in which the pollination is carefully controlled and is monitored. The resulting oilseeds formed on a plant resulting from the halfseed are harvested, planted, and are self-pollinated for a sufficient number of generations to achieve substantial genetic homogeneity. The genetic stabilization of the oilseed *Brassica napus* plant material enables the creation of plants having a reasonably predictable genotype which can be used as breeding or source material.

In accordance with the concept of the present invention, it additionally is essential that each of the female and male parent plants possesses at least one homozygous modified FAD-3 (i.e., linolate desaturase) gene pair that causes the expression of a reduced linolenic acid (i.e., alpha-linolenic acid) concentration in the endogenously formed oil of the seeds. Such modified FAD-3 gene pair can be obtained by genetic engineering or the mutagenesis of conventional *Brassica napus* germplasm (e.g., existing canola varieties) or can be selected from previously available sources that already incorporate the requisite FAD-3 gene modification. The modified FAD-3 gene pair can be present in either the A-genome or in the C-genome, and preferably is present in each of the these genomes. The modified FAD-3 gene pair likewise preferably is obtainable by mutagenesis. A reduced linolenic acid content of no more than 3 percent by weight based upon the total fatty acid content preferably is exhibited by each of the parent plants in the endogenously formed vegetable oil of the seeds. In a preferred embodiment, both the female parent and the male parent exhibit a linolenic acid (C18:3) content of approximately 1 to 3 percent by weight (e.g., 1 to 2 percent by weight) based upon the total fatty acid content.

Oilseed *Brassica napus* germplasm containing the requisite homozygous modified FAD-3 gene pair(s) that causes a reduced linolenic acid concentration in the endogenously formed oil of the seeds is known and is publicly available. For instance, rape germplasm possessing this trait has been available in Germany from the mid-1970's, and in North American since 1983. Representative commercially available rape varieties that include the genetic means for the expression of this low linolenic acid trait include STELLAR, and APOLLO. A particularly preferred source for the requisite FAD-3 gene pair for the expression of enhanced linolenic acid in the stated concentration is the STELLAR variety that was developed at the University of Manitoba, Manitoba, Canada, during 1987, following receipt of support from the Western Canola and Rapeseed Recommending Committee. Also, a particularly preferred source for the requisite FAD-3 gene pair for the expression of enhanced linolenic acid in the stated concentration is the APOLLO variety that was developed at the University of Manitoba, and was registered in Canada as No. 3,694 during February, 1992, following the receipt of support from the Western Canola and Rapeseed Recommending Committee.

*Brassica napus* seeds designated NS1973 and NS2037 and possessing the requisite modified FAD-2 gene pair solely in one genome as well as the modified FAD-3 gene pair suitable for use as the female parent in the process of the present invention were deposited under the terms of the Budapest Treaty at the American Type Culture Collection, 10801 University Boulevard, Manassas, Va., U.S.A. 20110-2209, on Jun. 25, 1998. A 2,500 seed deposit of NS1973 has been assigned ATCC Accession No. 209997. A 2,500 seed deposit of NS2037 has been assigned ATCC Accession No. 209994.

*Brassica napus* seeds designated 95SN-56605 and 95SN-56634 and possessing the requisite modified FAD-2 gene pair in both the A-genome and the C-genome as well as modified FAD-3 gene pair suitable for use as the male parent in the process of the present invention additionally were deposited under the terms of the Budapest Treaty at the American Type Culture Collection on Jun. 25, 1998. A 2,500 seed deposit of 95SN-56605 has been assigned ATCC Accession No. 209995. A 2,500 seed deposit of 95SN-56634 has been assigned ATCC Accession No. 209996.

When the parent plants are grown within pollinating proximity of each other in accordance with the process of the present invention, it is essential that self-pollination of the female parent plants be precluded. This can be done through the emasculation of the flowers at an early stage of flower development. Such impediment to self-pollination preferably is accomplished through the prevention of pollen formation on the female parent plants through any one of a variety of techniques that is inherent within the plant. Such female parent plants can incorporate some form of male sterility. For instance, male sterility can be cytoplasmic male sterility (i.e., genic-cytoplasmic), nuclear male sterility, molecular male sterility wherein a transgene inhibits microsporogenesis and/or pollen formation, or be produced by self-incompatability. In a particularly preferred embodiment the female parent plants possess cytoplasmic male sterility of the ogura (OGU) type and the male parent plants include a fertility restorer as available from Institut National de Recherche Agricole (INRA) of Rennes, France. See also in this regard the technology of International Publication Nos. WO92/05251 and WO98/027806 which is herein incorporated by reference.

The improved process of the present invention can be used to advantage to form single-cross *Brassica napus* $F_1$ hybrids. During such single-cross embodiment the parent plants can be grown as substantially homogeneous adjoining populations so as to well facilitate natural cross-pollination from the male parent plants to the female parent plants. The $F_1$ seed formed on the female parent plants next is selectively harvested by conventional means. One also has the option of growing the two parent plants during the formation of a single-cross hybrid in bulk and harvesting a composite seed blend of high oleic acid content consisting of $F_1$ hybrid seed, formed on the female parent and seed formed upon the male parent as the result of self-pollination. Alternatively, three-way crosses can be carried out wherein a single-cross $F_1$ hybrid is used as a female parent and is crossed with a different male parent that satisfies the fatty acid parameters for the female parent of the first cross. Here, assuming a bulk planting, the overall oleic acid content of the vegetable oil will be reduced over that of a simple single-cross hybrid; however, the seed yield will be further enhanced in view of the good agronomic performance of both parents when making the second cross. Also, the formation of double-cross hybrids can be carried out wherein the products of two different single-crosses are combined. Self-incompatibility can be used to particular advantage to prevent self-pollination of female parents when forming a double-cross hybrid. Here the final seed product will be a composite of more than one genotype wherein the overall oleic acid content is at least 80 percent by weight based upon the total fatty acid content.

The $F_1$ hybrid seeds made possible by the use of the technology of the present invention commonly exhibit an oleic acid concentration of approximately 80 to 86 percent by weight and a linolenic acid content of approximately 1 to 3 percent by weight based upon the total fatty acid content, and are capable of forming plants which following self-pollination and seed set yield a seed harvest bearing a vegetable oil having average oleic acid and linolenic acid concentrations within the specified ranges.

The improved process of the present invention makes possible the formation of *Brassica napus* $F_1$ hybrid seeds which when planted are capable of producing a crop in a yield that exceeds that of each parent used in the formation of the $F_1$ hybrid when each parent is pollinated by a pollen source possessing a genotype substantially the same as that of each parent and is grown under the same conditions. Additive gene action with respect to oleic acid production is achieved without sacrifice of agronomic characteristics. This good yield is made possible while making possible an oleic acid content in the vegetable oil of at least 80 percent (e.g., 80 to 86 percent) by weight based upon the total fatty acid content. Commonly, seed yields of equal to or greater than those of widely grown canola varieties which lack the modified fatty acid profile are made possible. In a preferred embodiment the yield exceeds that of the well-known Legend variety under the same growing conditions. The reference Legend variety was introduced by Svalöf AB during 1988 and is known and publicly available. Seeds of the Legend variety can be obtained from Svalöf-Weibull Canada Ltd., of Lindsay, Ontario, Canada.

The following Examples are presented as specific illustrations of the claimed invention. It should be understood, however, that the invention is not limited to the specific details set forth in the Examples.

EXAMPLE I

A *Brassica napus* line designated NS1973 was selected for use as the female parent. Such line was derived through crossing and pedigree selection in progeny generations from FA677M5-132 (ATCC Accession No. 40523). In the endogenously formed vegetable oil of NS1973 there was exhibited an average oleic acid (C18:1) content of 79.02 percent by weight and an average linolenic acid (C18:3) content of 1.65 percent by weight based upon the total fatty acid content. In this female parent the elevated oleic acid content was created through the presence of a homozygous modified FAD-2 gene pair solely in one genome that was formed through mutagenesis and the reduced linolenic acid content was created through the presence of at least one homozygous modified FAD-3 gene pair that was formed through mutagenesis. Seeds of NS1973 bear ATCC Accession No. 209997 as earlier discussed.

A *Brassica napus* line designated 95SN56605 was selected for use as the male parent. Such line was derived through crossing and pedigree selection in progeny generations from FA677M5-132 (ATCC Accession No. 40523). In the endogenously formed vegetable oil of 95SN56605 there was exhibited an average oleic acid (C18:1) content of 87.09 percent by weight and an average linolenic acid (C18:3) content of 1.64 percent by weight based upon the total fatty acid content. In this male parent the highly elevated oleic acid content was created through the presence of a homozygous modified FAD-2 gene pair in both the A-genome and the C-genome that was formed through mutagenesis and the reduced linolenic acid content was created through the presence of at least one homozygous modified FAD-3 gene pair that was formed through mutagenesis. Seeds of 95SN56605 bear ATCC Accession No. 209995 as previously discussed.

In order to determine parent yield potential, the parent lines were grown as a plot of twenty plants each in a replicated yield trial at Acton, Ontario, Canada, and were bagged to ensure self-pollination. The bags were removed at the end of flowering so that the fatty acid composition of the selfed seed would not be affected by an artificial bagged environment during the final portion of the seed filling when most of the lipid accumulation takes place. At maturity the selfed plants were harvested individually. Fatty acid and yield determinations were made. When determining yield the total weight of harvested seed was adjusted to 8.5 percent moisture. A value of 100 was assigned to the seed yield of the NS1973 female parent. On this scale, a seed yield of only 43 percent that of the female parent was found to form on the 95SN56605 male parent.

$F_1$ hybrid seeds and $F_2$ seeds were produced in a common field environment at the same location and were evaluated for yield and fatty acid composition. More specifically, the flowers of the NS1973 female parent were hand emasculated at an early stage of flower development according to the procedure described in Chapter 35 entitled "Rapeseed and Mustard" by R. K. Downey et al appearing at Pages 495 to 509 of "Hybridization of Crop Plants" edited by Walter R. Fehr and Henry H. Hadley (1980) in order to prevent the self-pollination of the female parent plants. At the appropriate stage in flower maturity, pollen was transferred by hand from the 95SN56605 male parent plants to the NS1973 female parent plants to accomplish fertilization. $F_1$ hybrid seeds were next produced on the fertilized NS1973 female parent plants which were selectively harvested and were analyzed for the fatty acid composition of the endogenously formed vegetable oil of the seeds.

The resulting $F_1$ hybrid seeds were found to exhibit an average elevated oleic acid content of 82.36 percent by weight and a reduced linolenic acid content of 1.59 percent by weight based upon the total fatty acid content. Also, the $F_1$ hybrid seed yield was found to be 127 percent of the female parent and exceeded that of each of the parent plants. Also, when the $F_1$ hybrid seeds were planted, they were found to exhibit good agronomic characteristics unlike the male parent plants.

EXAMPLE II

Example I was repeated with the exception that *Brassica napus* 95SN56634 (ATCC Accession No. 209996) was substituted for male parent 95SN56605. Such 95SN56634 line was derived through crossing and pedigree selection in progeny generations from FA677M5-132 (ATCC Accession No. 40523). In the endogenously formed vegetable oil of 95SN56634 there was exhibited an average oleic acid (C18:1) content of 86.57 percent by weight and an average linolenic acid (C18:3) content of 1.42 percent by weight based upon the total fatty acid content. The seed yield of the 95SN56634 male parent was found to be only 50 percent that of the female parent. The highly elevated average oleic acid content of the male parent was created through the presence of a homozygous modified FAD-2 gene pair in both the A-genome and the C-genome that was formed through mutagenesis and the reduced linolenic acid content was created through the presence of at least one homozygous modified FAD-3 gene pair that was formed through mutagenesis. The resulting $F_1$ hybrid seeds were found to exhibit an average elevated oleic acid content of 82.6 percent by weight and an average reduced linolenic acid content of 1.69 percent by weight based upon the total fatty acid content. Also, the $F_1$ hybrid seed yield was found to be 108 percent that of the female parent. When the $F_1$ hybrid seeds were planted, the resulting plants were found to exhibit good agronomic characteristics unlike the male parent plants.

EXAMPLE III

Example I was repeated with the exception that *Brassica napus* line NS2037 (ATCC Accession No. 209994) was substituted for female parent line NS1973 and *Brassica napus* line 95SN56634 was substituted for male parent line 95SN56605. Such NS2037 line was derived through crossing and pedigree selection in progeny generations from FA677M5-132 (ATCC Accession No. 40523). In the endogenously formed vegetable oil of NS2037 there was exhibited an average oleic acid (C18:1) content of 78.64 percent by weight and an average linolenic acid (C18:3) content of 1.52 percent by weight based upon the total fatty acid content. In such female parent the elevated oleic acid content was created through the presence of a homozygous modified FAD-2 gene pair solely in one genome that was formed through mutagenesis and the reduced linolenic acid content was created through the presence of at least one homozygous modified FAD-3 gene pair that was formed through mutagenesis. The $F_1$ hybrid seed was found to exhibit an average elevated oleic acid content of 82.3 percent by weight and an average reduced linolenic acid content of 1.51 percent by weight based upon the total fatty acid content. Also, the $F_1$ hybrid seed yield was found to be 150 percent that of the female parent and exceeded that of each of the parent plants. Also, when the $F_1$ hybrid plants were planted, the resulting plants were found to exhibit good agronomic characteristics unlike the male parent plants.

EXAMPLE IV

Example I was repeated with the exception that *Brassica napus* line NS2037(ATCC Accession No. 20994) utilized in Example III was substituted for female parent line NS1973. The $F_1$ hybrid seed was found to exhibit an average elevated oleic acid (C18:1) content of 82.69 percent by weight and an average reduced linolenic acid (C18:3) content of 1.46 percent by weight based upon the total fatty acid content. Also, the $F_1$ hybrid seed yield was found to be 119 percent that of the female parent. When $F_1$ hybrid plants were planted, the resulting plants were found to exhibit good agronomic characteristics unlike the male parent plants.

The homozygous modified FAD-2 and FAD-3 gene pairs present in the *Brassica napus* parent plants of all Examples can be readily transferred by conventional plant breeding to other *Brassica napus* germplasms which can likewise be used to carry out the process of the present invention. Also, the prevention of the self-pollination of the female parent plants when carrying out the process of the present invention can be expeditiously carried out on a larger scale by the use of various types of male sterility, etc., as previously discussed. Such techniques to preclude self-pollination of the female parent plants are already known and available to those skilled in plant breeding.

Although the invention has been described with preferred embodiments, it is to be understood that variations and modifications may be resorted to as will be apparent to those skilled in the art. Such variations and modifications are to be considered within the purview and scope of the claims appended hereto.

I claim:

1. A process for producing $F_1$ hybrid *Brassica napus* seeds comprising:

(a) planting in pollinating proximity in a planting area parent plants (i) and (ii), wherein parent (i) is a *Brassica napus* plant possessing solely in either the A-genome or the C-genome a homozygous modified FAD-2 gene pair obtained by mutagenesis that causes expression of an elevated oleic acid concentration in the endogenously formed oil of the seeds formed thereon, and further possesses at least one homozygous modified FAD-3 gene pair obtained by mutagenesis that causes the expression of a reduced linolenic acid concentration in the endogenously formed oil of said seeds, and wherein parent (ii) is a *Brassica napus* plant possessing in each of the A-genome and the C-genome a homozygous modified FAD-2 gene pair obtained by mutagenesis that causes the expression of an elevated oleic acid concentration in the endogenously formed oil of the seeds formed thereon whereby oleic acid is formed in the endogenously formed oil of said seeds in a greater concentration than in the seeds of parent (i) under the same growing conditions, and further possesses at least one homozygous modified FAD-3 gene pair obtained by mutagenesis that results in a reduced linolenic acid concentration in the endogenously formed oil of the seeds formed thereon;

(b) growing *Brassica napus* plants resulting from said planting of step (a);

(c) preventing self-pollination of the plants of parent (i);

(d) transferring pollen between said parent (ii) and said parent (i); and (e) harvesting $F_1$ hybrid seeds produced on plants of parent (i) that produce *Brassica napus* plants that upon self-pollination form seeds possessing an endogenously formed vegetable oil having an oleic acid concentration of at least 80 percent by weight and which exceeds that of parent (i), and a linolenic acid concentration of no more than 3 percent by weight, and wherein said resulting $F_1$ hybrid seeds when planted produce a crop in a yield that exceeds that of parent (i) and parent (ii) when each parent is pollinated by a pollen source possessing a genotype substantially the same as that of each parent plant and is grown under the same conditions.

2. The process according to claim 1 wherein parent plant (i) is male sterile.

3. The process according to claim 2 wherein parent plant (i) is cytoplasmic male sterile.

4. The process according to claim 2 wherein parent plant (i) and plant (ii) each is planted and grown in at least one substantially homogeneous adjoining population so as to facilitate natural cross pollination.

5. The process according to claim 1 wherein said parent plant (i) possesses a homozygous modified FAD-2 gene pair that is present solely in either the A-genome or the C-genome which produces, when pollinated by a pollen source possessing substantially the same genotype, an enhanced oleic acid concentration in the endogenously formed oil of seeds formed thereon which exceeds that of the 'Profit' variety which possesses an unmodified FAD-2 gene pair by at least 14 percent by weight based upon the total fatty acid content when grown under the same conditions.

6. The process according to claim 1 wherein said parent plant (ii) possesses a homozygous modified FAD-2 gene pair in each of the A-genome and the C-genome which produce, when pollinated by a pollen source possessing substantially the same genotype, an enhanced oleic acid concentration in the endogenously formed oil of seeds formed thereon which exceeds that of the 'Profit' variety which possesses an unmodified FAD-2 gene pair by at least 20 percent by weight based upon the total fatty acid content when grown under the same conditions.

7. The process according to claim 1 wherein said parent plant (i) exhibits in the seeds formed thereon when pollinated by a pollen source possessing substantially the same genotype an oleic acid concentration of approximately 77 to 79 percent by weight and a linolenic acid concentration of approximately 1 to 3 percent by weight based upon the total fatty acid content when grown under the same conditions, and said parent plant (ii) exhibits in the seeds formed thereon when pollinated by a pollen source possessing substantially the same genotype an oleic acid concentration of approximately 85 to 89 percent by weight and a linolenic acid concentration of approximately 1 to 2 percent by weight based upon the total fatty acid content when grown under the same conditions.

8. The process according to claim 1 wherein said $F_1$ hybrid seeds that are harvested in step (e) exhibit an oleic acid concentration of approximately 80 to 86 percent by weight and a linolenic acid content of approximately 1 to 3 percent by weight based upon the total fatty acid content.

9. The process according to claim 1 wherein said $F_1$ hybrid seeds are harvested in step (e) that produce a crop in a yield that exceeds that of the 'Legend' variety under the same growing conditions.

10. A process for producing $F_1$ hybrid *Brassica napus* seeds comprising:

(a) planting in pollinating proximity parent plants (i) and (ii), wherein parent (i) is a *Brassica napus* plant possessing solely in either the A-genome or the C-genome a homozygous modified FAD-2 gene pair obtained by mutagenesis that results in an elevated oleic acid production in the endogenously formed oil of the seeds formed thereon which exceeds that of the 'Profit' variety, which possesses an unmodified FAD-2 gene pair by at least 14 percent by weight based upon the total fatty acid content under the same growing conditions; and at least one homozygous modified FAD-3 gene pair obtained by mutagenesis that results in a reduced linolenic acid production in the endogenously formed oil of the seeds formed thereon of no more than 3 percent by weight based upon the total fatty acid content, and wherein parent (ii) is a *Brassica napus* plant possessing in each of the A-genome and the C-genome a homozygous modified FAD-2 gene pair obtained by mutagenesis that results in an elevated oleic acid production in the endogenously formed oil of the seeds formed thereon which exceeds that of the 'Profit' variety, which possesses an unmodified FAD-2 gene pair, by at least 20 percent by weight based upon the total fatty acid content and forms oleic acid in the endogenously formed oil of said seeds in a greater concentration than parent (i) under the same growing conditions; and a homozygous modified FAD-3 gene pair obtained by mutagenesis that results in a reduced linolenic acid content in the endogenously formed oil of the seeds formed thereon of no more than 3 percent by weight based upon the total fatty acid content;

(b) growing *Brassica napus* plants resulting from said planting of step (a);

(c) preventing self-pollination of the plants of parent (i);

(d) transferring pollen between said parent (ii) and said parent (i); and (e) harvesting $F_1$ hybrid seeds produced on plants of parent (i) that produce *Brassica napus* plants that upon self-pollination form seeds possessing an endogenously formed vegetable oil having an oleic acid concentration of at least 80 percent by weight and which exceeds that of parent (i), and a linolenic acid concentration of no more than 3 percent by weight, and wherein said resulting $F_1$ hybrid seeds when planted produce a crop in a yield that exceeds that of parent (i) and parent (ii) when each is pollinated by a pollen source possessing a genotype substantially the same as that of each parent plant and is grown under the same conditions.

11. The process according to claim 10 wherein said parent plant (i) is male sterile.

12. The process according to claim 11 wherein parent plant (i) is cytoplasmic male sterile.

13. The process according to claim 11 wherein parent plant (i) and parent plant (ii) each is planted and grown in at least one substantially homogeneous adjoining population so as to facilitate natural cross pollination.

14. The process according to claim 10 wherein said parent plant (i) exhibits in the seeds formed thereon when pollinated by a pollen source possessing substantially the same genotype an oleic acid concentration of approximately 77 to 79 percent by weight and a linolenic acid concentration of approximately 1 to 3 percent by weight based upon the total fatty acid content when grown under the same conditions, and parent plant (ii) exhibits in the seeds formed when pollinated by a pollen source possessing substantially the same genotype an oleic acid concentration of approximately 85 to 89 percent by weight and a linolenic acid concentration of approximately 1 to 3 percent by weight based upon the total fatty acid content when grown under the same conditions.

15. The process according to claim 10 wherein said $F_1$ hybrid seeds that are harvested in step (e) exhibit an oleic acid concentration of approximately 80 to 86 percent by weight and a linolenic acid content of approximately 1 to 3 percent by weight based upon the total fatty acid content, and are capable of forming plants which upon self-pollination which produce a crop having average oleic acid and linolenic acid concentrations within the specified ranges.

16. The process according to claim 10 wherein said $F_1$ hybrid seeds are harvested in step (e) produce a crop in a yield that exceeds that of the 'Legend' variety under the same growing conditions.

* * * * *